(12) United States Patent
Allegrini et al.

(10) Patent No.: US 8,461,190 B2
(45) Date of Patent: Jun. 11, 2013

(54) PROCESS FOR THE PURIFICATION OF RUFINAMIDE

(75) Inventors: Pietro Allegrini, San Donato Milanese (IT); Dario Pastorello, Milan (IT); Gabriele Razzetti, Sesto San Giovanni (IT)

(73) Assignee: Dipharma Francis S.r.L., Baranzate (MI) (IT)

( * ) Notice: Subject to any disclaimer, the term of this patent is extended or adjusted under 35 U.S.C. 154(b) by 0 days.

(21) Appl. No.: 13/451,651

(22) Filed: Apr. 20, 2012

(65) Prior Publication Data

US 2012/0277443 A1  Nov. 1, 2012

(30) Foreign Application Priority Data

Apr. 29, 2011 (IT) .............................. MI2011A0718

(51) Int. Cl.
*A61K 31/41* (2006.01)
*C07D 249/00* (2006.01)

(52) U.S. Cl.
USPC ......................................... 514/359; 548/255

(58) Field of Classification Search
USPC ........................................... 514/359; 548/255
See application file for complete search history.

(56) References Cited

U.S. PATENT DOCUMENTS

| | | | |
|---|---|---|---|
| 4,789,680 A * | 12/1988 | Meier | 514/359 |
| 2001/0037029 A1 | 11/2001 | Portmann et al. | |
| 2010/0234616 A1 | 9/2010 | Attolino et al. | |
| 2011/0034523 A1 | 2/2011 | Razzetti et al. | |

FOREIGN PATENT DOCUMENTS

| | | |
|---|---|---|
| EP | 199262 A2 | 10/1986 |
| WO | 9856772 A1 | 12/1998 |
| WO | 9856773 A1 | 12/1998 |

* cited by examiner

*Primary Examiner* — Susannah Chung
(74) *Attorney, Agent, or Firm* — Rothwell, Figg, Ernst & Manbeck, P.C.

(57) ABSTRACT

A process for purifying Rufinamide, comprising:
a) providing a dispersion of crude 1-[(2,6-difluorophenyl)methyl]-1H-1,2,3-triazole-4-carboxamide in a solvent mixture containing at least a carboxylic acid, and dissolving it;
b) slowly cooling the solution to precipitate Rufinamide crystalline form A; and
c) recovering the solid.

17 Claims, 3 Drawing Sheets

PROCESS FOR THE PURIFICATION OF RUFINAMIDE

FIELD OF THE INVENTION

Figure 1:
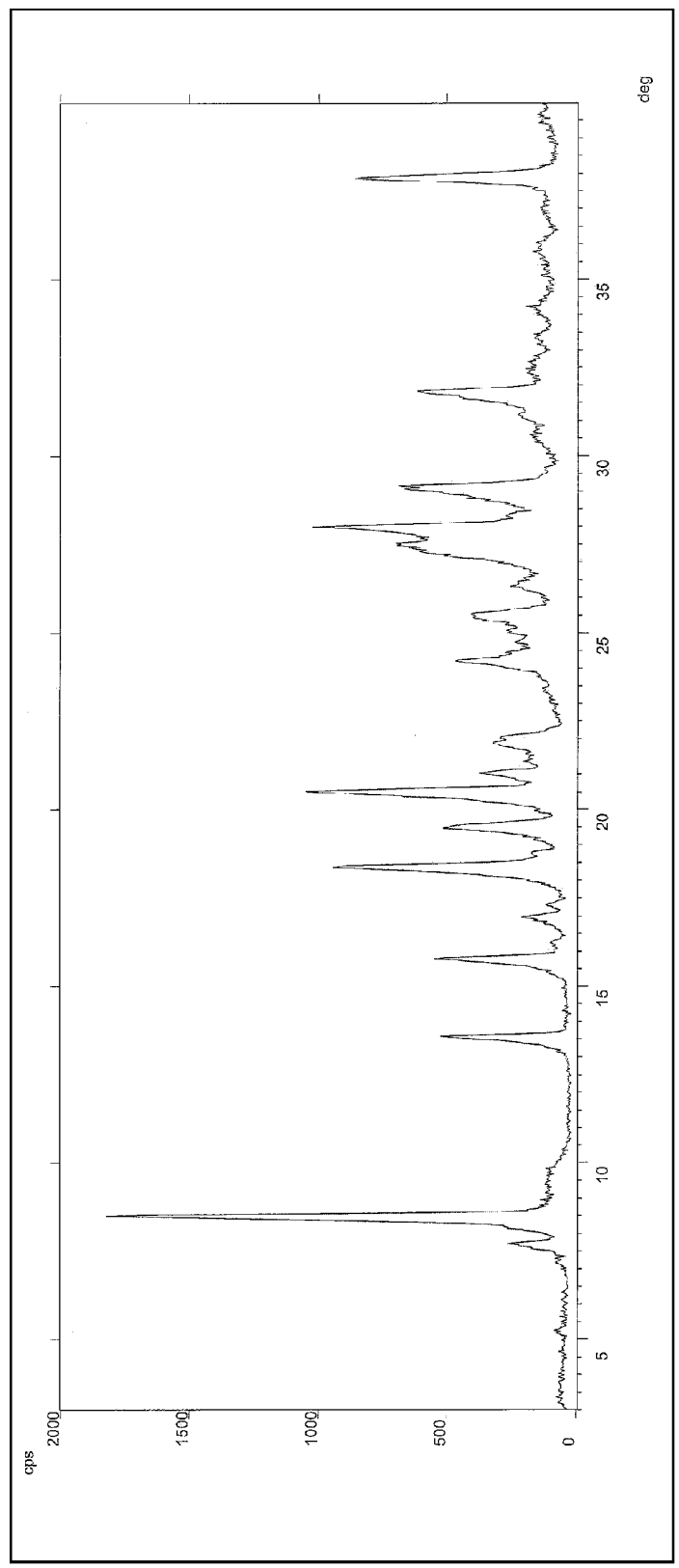

The present invention relates to a process for the purification of 1-[(2,6-difluorophenyl)methyl]-1H-1,2,3-triazole-4-carboxamide (Rufinamide) by crystallization to obtain Rufinamide in the crystalline form, designated as Form A, with a high purity degree.

TECHNOLOGICAL BACKGROUND

1-[(2,6-Difluorophenyl)methyl]-1H-1,2,3-triazole-4-carboxamide, i.e. Rufinamide, is an anticonvulsant used in combination with other antiepileptic drugs in the treatment of a rare form of epilepsy, named Lennox-Gastaut syndrome.

Rufinamide, having formula (I), is known from EP 199262.

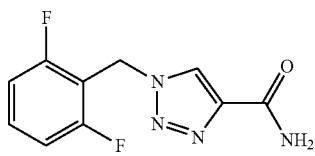

(I)

The chemical name 1-[(2,6-difluorophenyl)methyl]-1H-1,2,3-triazole-4carboxamide and the term Rufinamide are herein used interchangably, both in the disclosure and in the claims of the present application.

Various crystalline modifications of Rufinamide are known, for example the crystalline forms A and A' are known from WO 98/56772, the forms B and C are known from EP 994863, and the forms α and β from US 2011/0034523.

WO98/56772 teaches that the polymorphic Form A, which is the more stable, can be obtained by precipitation from different solvents or mixtures thereof, for example water, methanol, ethanol or a methanol/formic acid mixture, in which the product 1-[(2,6-difluorophenyl)methyl]-1H-1,2,3-triazole-4-carboxamide is poorly soluble.

WO 98/56772 discloses the preparation of the crystalline Form C of Rufinamide through rapid crystallization from acetic acid, in which Rufinamide is moderately soluble, typically by cooling the solution over about 8 minutes, with a yield of about 67%.

As known, the synthesis processes commonly used to manufacture Rufinamide provide it in admixture with varying amounts of impurities, such as the ester of formula (II) and the acid of formula (III)

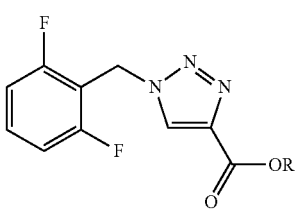

(II)

-continued

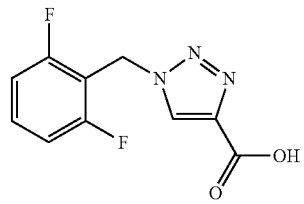

(III)

wherein R is an alkyl group, typically $C_1$-$C_6$ alkyl.

There is therefore the need for a process for the purification of Rufinamide, which provides an API (finished product) with high purity level and is industrially applicable.

SUMMARY OF THE INVENTION

An alternative process for the crystallization of Rufinamide has now been found, which allows one to obtain its stable crystalline modification Form A. Moreover, this novel crystallization process surprisingly proved to be also an effective procedure for the purification of Rufinamide, providing indeed an API with high purity, typically ≧99.95% HPLC.

BRIEF DESCRIPTION OF THE FIGURES AND ANALYTICAL METHODS

The crystalline Form A of Rufinamide was characterized by X-ray powder diffraction (XRPD), by $^1$H-NMR nuclear magnetic resonance spectrometer; by Differential Scanning Calorimetry (DSC); and by Infrared Spectrophotometry (FT-IR). The water content was determined by titration according to the Karl-Fischer technique.

The XRPD spectrum was recorded with an automatic diffractometer for powders and liquids APD-2000 (Ital-Structures) under the following operative conditions: Bragg-Brentano geometry, radiation CuKα ($\lambda$=1.5418 Å), scanning with angular interval 3-40° in 2θ with angular step of 0.03° for a time of 1 sec. $^1$H-NMR spectra were recorded with a Varian Mercury 300 spectrometer using DMSO-d6 as the solvent.

DSC thermograms were recorded with Mettler-Toledo DSC 822e differential scansion calorimeter, under the following operative conditions: open aluminium capsule, 30-300° C. interval at the rate of 10° C./min, with nitrogen as purging gas (80 ml/min).

The IR spectrum was recorded with a Perkin-Elmer Paragon 500 spectrophotometer for 16 scannings between 4000 and 650 $cm^{-1}$.

FIG. 1: XRPD spectrum of Rufinamide crystalline Form A; wherein the main peaks are located at 7.68; 8.46; 13.56; 15.75; 16.95; 18.36; 19.47; 20.49; 24.18; 25.47° in 2θ (±0.2°)

Figure 2:
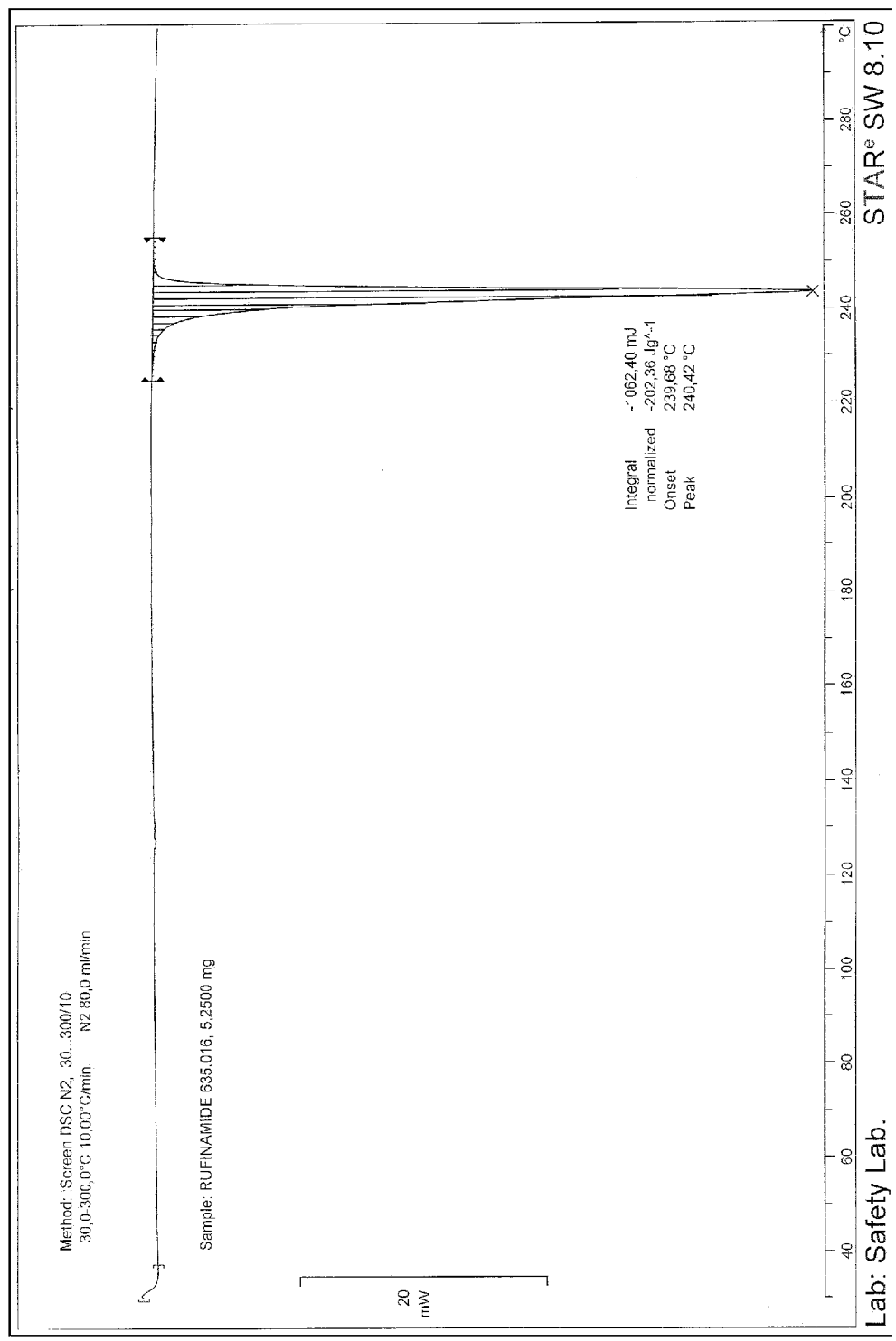

FIG. 2: DSC thermogram of Rufinamide crystalline Form A

Figure 3:
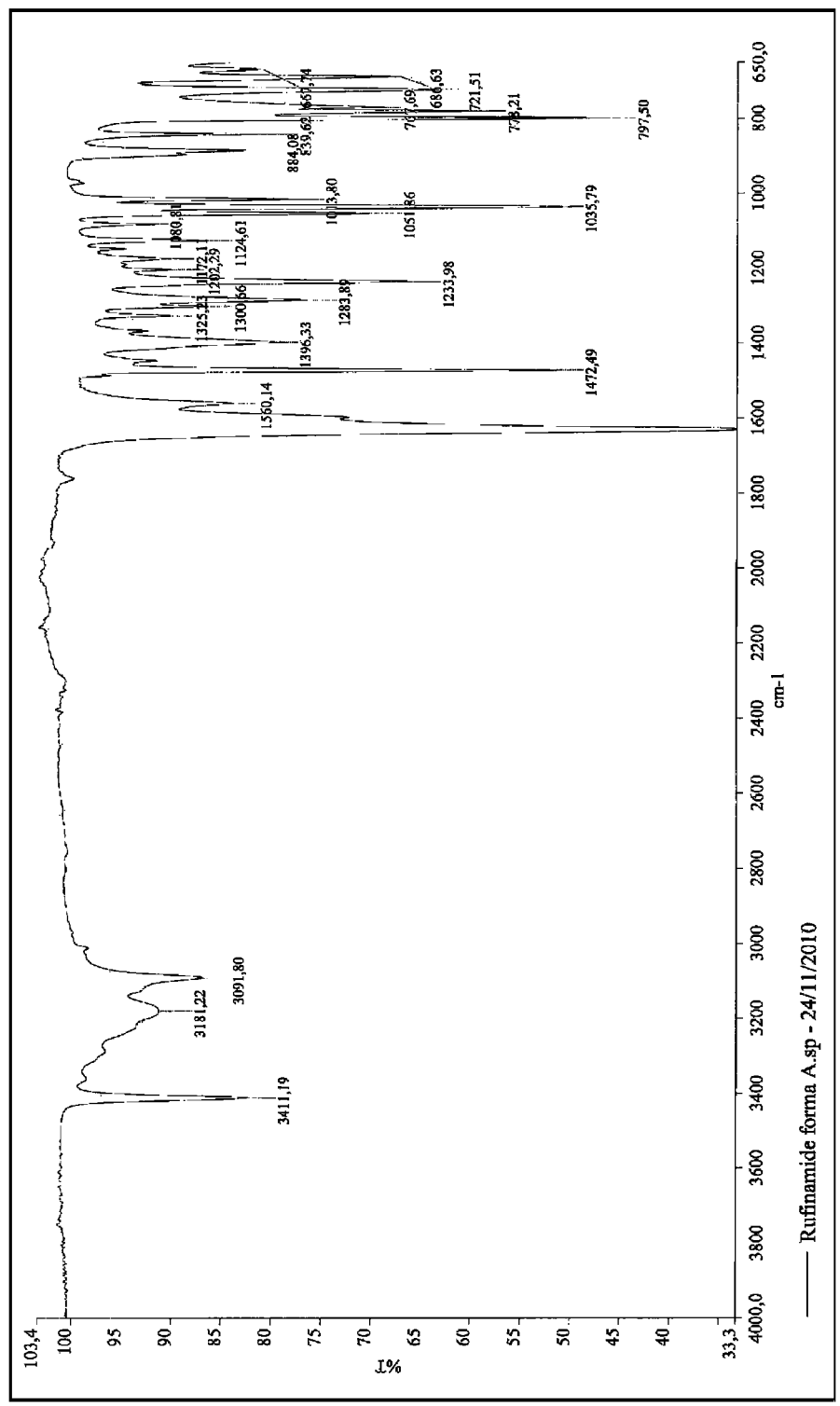

FIG. 3: FT-IR spectrum of Rufinamide crystalline Form A

DETAILED DISCLOSURE OF THE INVENTION

In a first aspect, the present invention relates to a novel process for the purification of Rufinamide, comprising:
a) providing a dispersion of crude 1-[(2,6-difluorophenyl)methyl]-1H-1,2,3-triazole-4-carboxamide in a solvent containing at least a carboxylic acid, and dissolving the crude;
b) slowly cooling the solution to obtain Rufinamide crystalline Form A; and
c) recovering the solid product.

Rufinamide, which can be purified according to the process of the present invention, can be any crude product as obtainable according to various methods for its preparation, for example according to EP 199262.

The concentration of crude Rufinamide in the starting dispersion can range between about 2 and 50% w/w, preferably between about 10 and 15% w/w.

The solvent is at least a carboxylic acid or a mixture of two or more, typically two or three, carboxylic acids. Preferably it is one carboxylic acid.

The carboxylic acid, which can be aliphatic or aromatic, can be for example a $C_2$-$C_5$ carboxylic acid or benzoic acid, optionally substituted with one or more, preferably one to three, halogen atoms for example independently chosen from fluorine and chlorine. Typically said aliphatic carboxylic acid is acetic acid, propionic acid, trifluoroacetic acid or a mixture thereof.

Preferably the carboxylic acid is acetic acid, trifluoroacetic acid or a mixture thereof, more preferably it is glacial acetic acid.

The dissolution of crude 1-[(2,6-difluorophenyl)methyl]-1H-1,2,3-triazole-4-carboxamide in the solvent mixture can be performed by heating the dispersion To a temperature of up to about 100° C., typically at about 90-95° C., to obtain its complete dissolution.

The cooling of the solution, to precipitate Rufinamide crystalline Form A, can be performed in a time ranging from about one hour to about 10 hours, preferably between about 5 and 7 hours, to bring the temperature of the mixture to about 17-25° C., preferably about 20° C.

According to a further object of the invention, an antisolvent can be added to the solution of 1-[(2,6-difluorophenyl)methyl]-1H-1,2,3-triazole-4-carboxamide before, after or substantially during the cooling step.

The antisolvent is preferably a polar protic solvent, for example water or a $C_1$-$C_4$ alkanol, typically methanol, ethanol or isopropanol; a ketone, typically a $C_2$-$C_4$ ketone, for example acetone; an ester, typically a $C_1$-$C_5$ alkyl ester of an aliphatic $C_1$-$C_5$ carboxylic acid, for example ethyl acetate; and an aliphatic or aromatic hydrocarbon, for example hexane, heptane or toluene; or a mixture of two or more, preferably two or three, of said antisolvents.

According to a preferred embodiment of the invention, the formation of the crystalline Form A of Rufinamide can be obtained by a process, wherein above described step b) comprises:
  d) cooling the solution of 1-[(2,6-difluorophenyl)methyl]-1H-1,2,3-triazole-4-carboxamide to a temperature of about 60-70° C., preferably about 65-70° C., over a time of at least 1-3 hours, preferably about 2 hours, to obtain a precipitate;
  e) heating the mixture containing the precipitate to a temperature of about 75-80° C., for at least 1-3 hours, preferably about one hour, to fluidify the mixture; and
  f) cooling the mixture thus obtained, in a time ranging from about one hour to 10 hours, preferably from about 5 to 7 hours, to bring the temperature of the mixture to about 17- 25° C., preferably to about 20° C., to precipitate Rufinamide crystalline Form A.

The recovery of the solid, consisting of Rufinamide crystalline Form A, from the final dispersion, can be effected with a known technique, for example by filtration or centrifugation, preferably by filtration.

The resulting Rufinamide crystalline Form A has a water content ranging from 0 to about 1% w/w, preferably from about 0.1 to 0.5%, so that it can be defined as substantially anhydrous.

The size of the crystals of Rufinamide Form A, as obtainable according to the invention, is characterized by a $D_{50}$ value ranging from about 25 to 250 μm. If desired, said value can be reduced by micronisation or fine grinding.

Rufinamide crystalline Form A, as obtainable according to the invention, has high purity degree, typically ≧99.95% HPLC, so that the ester of formula (II) and the acid of formula (III), as defined above, if present, are present in an amount lower than or equal to 0.03%, preferably lower than or equal to 0.01% HPLC.

According to a further aspect, the invention provides a composition containing Rufinamide crystalline Form A, with purity ≧99.95% HPLC, and an amount lower than or equal to 0.03% HPLC, preferably lower than or equal to 0.01% HPLC, of the ester of formula (II) and/or of the acid of formula (III), having the following formulae

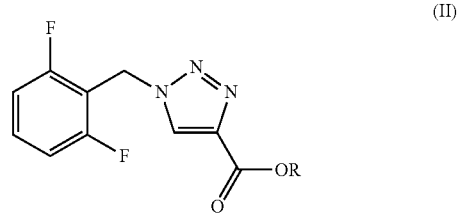

(II)

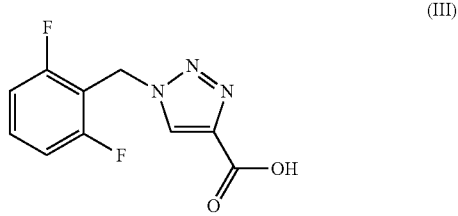

(III)

The following examples illustrate the invention.

EXAMPLE 1

Purification of Rufinamide 100.0 g of crude Rufinamide is suspended in 800 ml of acetic acid. The mixture is heated to 90-95° C. to complete dissolution of the solid, then cooled to 70° C., in about 2 hours, to obtain an abundant precipitation of the solid. The temperature is brought again to about 76° C. and the mixture is fluidized for at least one hour, then cooled down to 15-20° C. in 5-6 hours, and the white solid is recovered by pump filtration on Bückner. After drying in a static dryer at about 60° C. for 16 hours, 85 g of product is obtained. Yield: 85%; HPLC purity: >99.95%.

XRPD: main peaks are located at 7.68; 8.46; 13.56; 15.75; 16.95; 18.36; 19.47; 20.49; 24.18; 25.47° in 2θ (±0.2°)

$^1$H-NMR (in DMSO): s (2H), 5.71 ppm; m (2H), 7.14-7.19 ppm; m+bs (2H), 7.44-7.56 ppm; bs (1H), 7.81 ppm; s (1H), 8.53 ppm.

EXAMPLE 2

Purification of Rufinamide 10.0 g of crude Rufinamide is suspended in 80 ml of acetic acid. The mixture is then heated to 90-95° C. to complete dissolution of the solid. The mixture is cooled down to 15-20° C. in 5-6 hours, then 40 ml of water is added and left under stirring for at least a further hour. The white solid is recovered by pump filtration on Bückner. After drying in a static dryer at 60° C. for 16 hours, 9.1 g of product is obtained. Yield: 91%; HPLC purity: >99.95%. The analytical results confirmed the obtained crystalline product is Form A.

EXAMPLE 3

Purification of Rufinamide 1.0 g of crude Rufinamide is suspended in 10 ml of acetic acid. The mixture is then heated to 90-95° C. until complete dissolution of the solid. 60 ml of toluene are drop wise added, to promote crystallization. The mixture is cooled down to 15-20° C. in 5 hours, then the solid is recovered by pump filtration. After drying in a static dryer at 60° C. for 12 hours, 0.73 g of product is obtained. Yield: 73%; HPLC purity: >99.95%. The analytical results confirmed the obtained crystalline product is Form A.

EXAMPLE 4

Purification of Rufinamide 66.0 Kg of crude Rufinamide (purity: 99.89%) are suspended in 528 l of acetic acid. The mixture is then heated to 95-100° C. until complete dissolution of the solid. The mixture is cooled down to 70° C., in about 1 hour, to obtain an abundant precipitation of the solid. The temperature is brought again to about 70-80° C. and the mixture is fluidized for 2-3 hours, then cooled down to 15-20° C. in 5-6 hours, and the solid is recovered by centrifugation. After drying under vacuum at about 70-75° C. for 12 hours, 55.8 kg of product is obtained. Yield: 84.5%; purity HPLC: >99.95%. The analytical results confirmed the obtained crystalline product is Form A.

The invention claimed is:

1. A process for purifying Rufinamide, comprising:
   a) providing a dispersion of crude 1-[(2,6-difluorophenyl)methyl]-1H-1,2,3-triazole-4-carboxamide in a solvent comprising at least an optionally substituted $C_2$-$C_5$ carboxylic acid or benzoic acid, and dissolving the crude 1-[(2,6-difluorophenyl)methyl]-1H-1,2,3-triazole-4-carboxamide in the solvent;
   b) cooling the resulting solution for a time ranging from about one hour to about 10 hours to obtain Rufinamide crystalline Form A and
   c) recovering the solid product which has an XRPD wherein the main peaks are located at 7.68; 8.46; 13.56; 15.75; 16.95; 18.36; 19.47; 20.49; 24.18; 25.47° in 2θ (±0.2°); and characterized by a XRPD spectrum as shown in FIG. 1 and a DSC as shown in FIG. 2.

2. The process according to claim 1, wherein the concentration of crude 1-[(2,6-difluorophenyl)methyl]-1H-1,2,3-triazole-4-carboxamide in the dispersion is between about 2 and about 50% w/w.

3. The process according to claim 1 wherein the concentration of crude 1-[(2,6-difluorophenyl)methyl]-1H-1,2,3-triazole-4-carboxamide in the dispersion is between about 10 and about 15% w/w.

4. The process according to claim 1, wherein the $C_2$-$C_5$ carboxylic acid is acetic acid, propionic acid, trifluoroacetic acid, or a mixture thereof.

5. The process according to claim 4 wherein the carboxylic acid is glacial acetic acid.

6. The process according to claim 1, wherein the dissolution of crude 1-[(2,6-difluorophenyl)methyl]-1H-1,2,3-triazole-4-carboxamide in the solvent mixture is performed by heating the dispersion up to a temperature of no more than about 100° C.

7. The process according to claim 6 wherein the dispersion is heated to about 90-95° C.

8. The process according to claim 1, wherein the cooling of the solution is performed over a time ranging from about 5 to about 7 hours.

9. The process according to claim 1, wherein the cooling of the solution brings the mixture to a temperature of about 17-25° C.

10. The process according to claim 1 wherein the cooling of the solution brings the mixture to a temperature of about 20° C.

11. The process according to claim 1, wherein an antisolvent, selected from the group consisting of a polar protic solvent; a ketone; an ester; an aliphatic or aromatic hydrocarbon; or a mixture of at least two of said antisolvents, is added to the solution of 1-[(2,6-difluorophenyl)methyl]-1H-1,2,3-triazole-4-carboxamide before, after or substantially during the cooling step.

12. The process according to claim 11, wherein the antisolvent is water or toluene.

13. The process according to claim 1, wherein step b) comprises:
   d) cooling the solution of 1-[(2,6-difluorophenyl)methyl]-1H-1,2,3-triazole-4-carboxamide to a temperature of about 60-70° C., over a time of at least 1-3 hours, to obtain a precipitate;
   e) heating the mixture containing the precipitate to a temperature of about 75-80° C., for at least about 1-3 hours; and
   f) cooling the mixture over a time of about one hour to about 10 hours to bring the temperature of the mixture to about 17-25° C., to precipitate Rufinamide crystalline Form A.

14. The process according to claim 13 wherein the solution of step d) is cooled to a temperature of about 65-70° C. over about 2 hours.

15. The process according to claim 13 wherein the mixture of step f) is cooled over about 5-7 hours to bring the temperature of the mixture to about 20° C.

16. The process according to claim 11, wherein said mixture of antisolvents contains two or three of said antisolvents.

17. The process according to claim 13, wherein in step e) the mixture containing the precipitate is heated for about one hour.

* * * * *